United States Patent [19]

Glastra

[11] Patent Number: 5,741,324
[45] Date of Patent: Apr. 21, 1998

[54] METHOD FOR MANUFACTURING A STENT AND STENT OBTAINED WITH SAID METHOD

[75] Inventor: Hendrik Glastra, Enschede, Netherlands

[73] Assignee: Cordis Corporation, Miami, Fla.

[21] Appl. No.: 590,903

[22] Filed: Jan. 24, 1996

[30] Foreign Application Priority Data

Jan. 26, 1995 [DE] Germany .................................. 9500147

[51] Int. Cl.[6] .................................................. A61F 2/06
[52] U.S. Cl. .................................................. 623/1
[58] Field of Search .................................... 623/1; 600/36

[56] References Cited

U.S. PATENT DOCUMENTS 5,100,429 3/1992 Sinofsky et al. .

FOREIGN PATENT DOCUMENTS 0617930 10/1994 European Pat. Off. .

OTHER PUBLICATIONS

Dutch Patent Office Search Report for Dutch Patent Application 9500147.

Primary Examiner—John G. Weiss
Assistant Examiner—John M. Black
Attorney, Agent, or Firm—Lockwood, Alex, Fitzgibbon & Cummings

[57] ABSTRACT

A method for forming a stent includes forming a sleeve from a biocompatible material, curling one end of the sleeve upon itself to form a skirt extending for a preselected length along and above the sleeve, the skirt and sleeve cooperating to define an annular space therebetween, filling the space with a curable material curling the opposite end of the sleeve onto the skirt to completely enclose the curable material and fixing the opposite end to the skirt to seal the curable material therein.

20 Claims, 5 Drawing Sheets

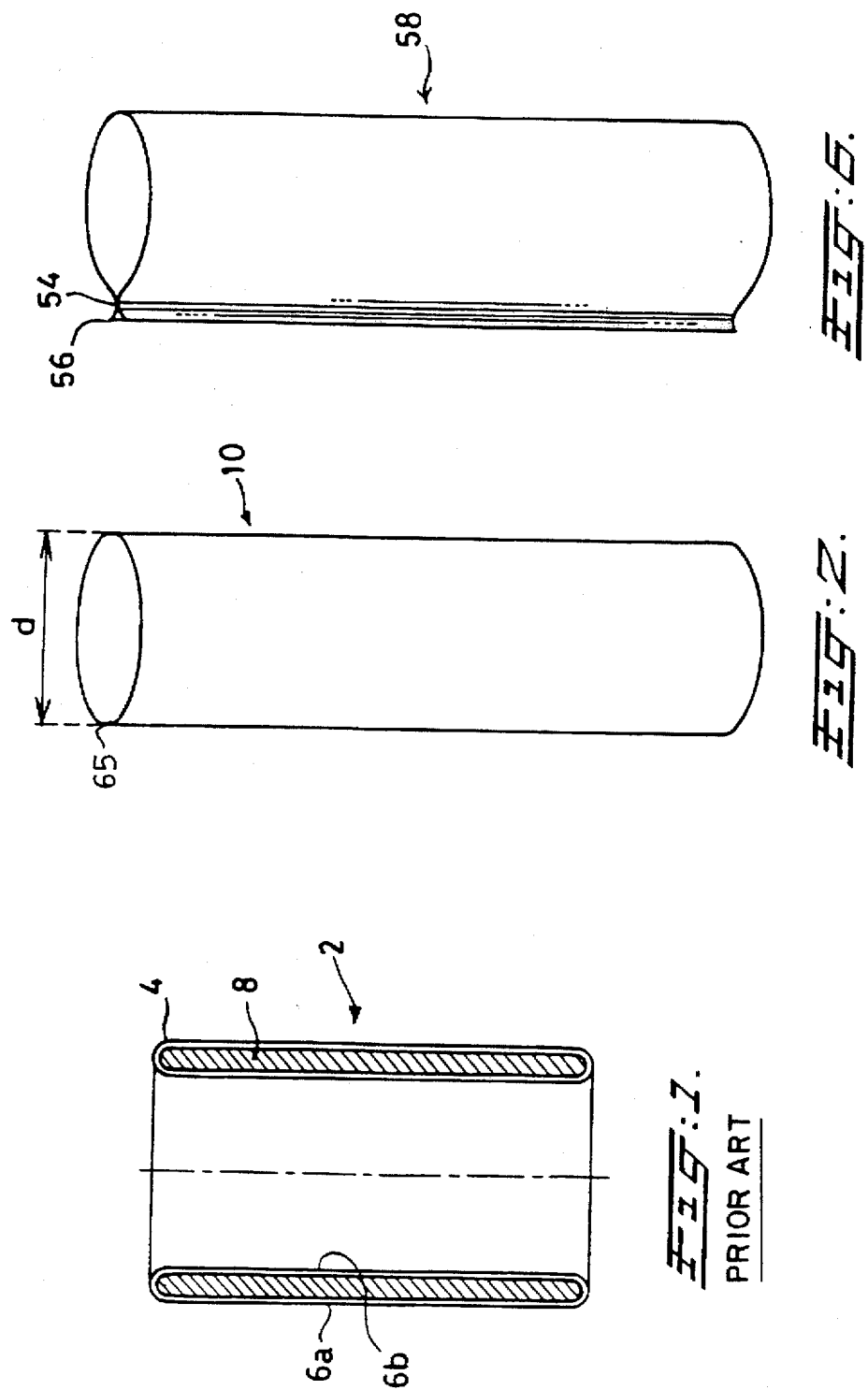

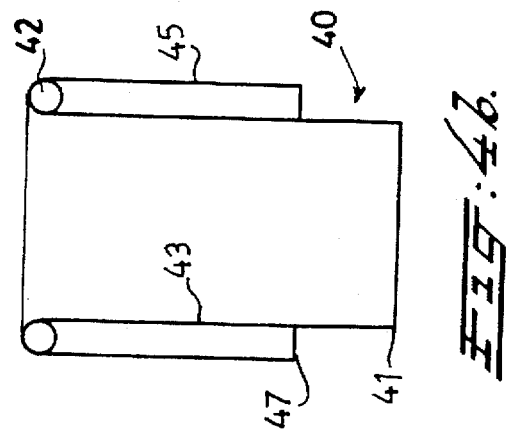
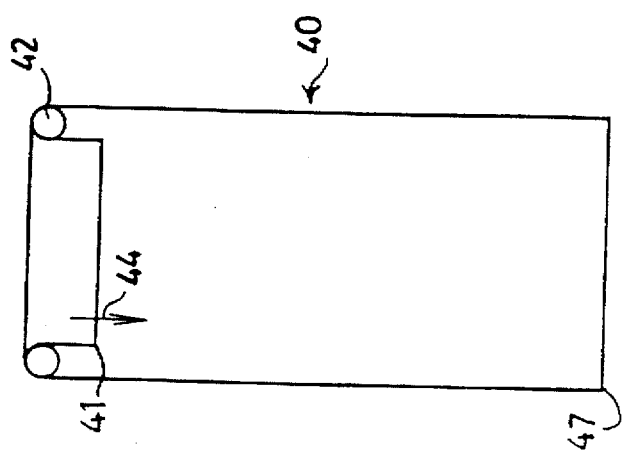

METHOD FOR MANUFACTURING A STENT AND STENT OBTAINED WITH SAID METHOD

BACKGROUND AND SUMMARY OF THE INVENTION

The present invention generally relates to the manufacture of implantable stents, and more particularly to a method of manufacturing an implantable stent from a thin foil or film of biocompatible material by forming a double-wall sleeve having a radiation-curable material enclosed between the walls of the sleeve.

Stents are widely used in the repair of compromised blood vessels. Stents may take a variety of shapes and may be formed from a variety of materials. In the simplest sense, a stent typically takes the form of a hollow tube and in more sophisticated forms, the stent may take the form of a tube formed from either a lattice or an open-weave mesh.

Stents are also known to be formed from curable materials which have a initial plastic form which permits them to be inserted into the blood vessel. The curable material is then subjected to a curing agent and the material cures in place within the blood vessel to form a reliable stent. Such a stent and a method for manufacturing thereof are described in my copending European patent application, EP-A-0 617 930.

The present invention is directed to a method of forming a stent in a manner so that stents of different sizes can be formed swiftly and accurately by an industrial manufacturing process.

It is a general object of the present invention to provide a method for forming an implantable stent by forming a envelope-like sleeve, filling the sleeve with a curable material and closing the sleeve to form a stent of any predesired length and/or diameter.

Another object of the present invention is to provide a method for manufacturing a stent by first forming a single wall sleeve from a biocompatible material, curling one end of the sleeve upon itself to form a skirt of predesired length extending upon the sleeve toward the opposite end thereof while leaving the opposite end of the sleeve free and extending away from the one end curled upon the sleeve, the skirt and sleeve cooperating to define a double-wall portion of the sleeve having an annular space disposed between the skirt and sleeve, filling the annular space so formed with a curable material, curling the opposite end of the sleeve up and over a portion of the skirt to enclose the curable material within the sleeve and fixing the opposite end of the sleeve to the skirt.

In one aspect of the present invention, a method is provided for forming a stent which includes the steps of: forming a sleeve from a foil material with a diameter related to the diameter of the stent to be formed; folding back a portion of the sleeve onto itself to form a double-walled sleeve wherein the distance between the two walls is related to the length of the stent to be formed, the folded sleeve portion including a single thickness extent of foil adjoining the double walled portion; arranging a curable material in the space between both walls of the double-walled sleeve portion; and folding back the single thickness extent over the outer wall of the double-walled sleeve portion and connecting it to the outer wall.

The method steps according to the invention can be performed mechanically by means of simple auxiliary tools so that the stents may be easily produced in a variety of lengths and diameters.

One benefit of the methods of the present invention is that it becomes possible to obtain stents of larger sizes in a simple and reliable manner. With such stents, it is possible to repair or reinforce blood vessels over a larger extent, e.g. 10 to 15 cm. Moreover, the desired local stiffness of the stent can be varied over the length of the stent by applying a more or less thick layer of curable material received on a supporting material.

These and other objects, features and advantages of the present invention will be clearly understood through a consideration of the following detailed description.

BRIEF DESCRIPTION OF THE DRAWINGS

In the course of the following detailed description, reference will be frequently made to the accompanying drawings in which:

FIG. 1 shows a longitudinal section of a prior art stent;

FIG. 2 is a perspective view of a sleeve of biocompatible material used in forming the stent according to the methods of the present invention;

FIGS. 4a–4b show schematically and in longitudinal section two alternate steps the method of the present invention in which the one end of the sleeve is drawn inwardly upon the sleeve and the one end is folded upon the opposite end to close off the sleeve;

FIG. 6 is a perspective representation of the basic sleeve obtained according to FIGS. 5a–5c.

DETAILED DESCRIPTION OF THE INVENTION

Figure 3B:
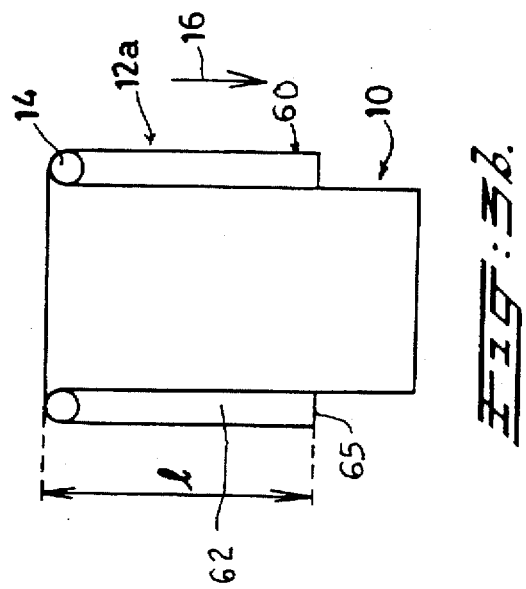
FIGS. 3a–3e show schematically and in longitudinal section, several steps of the method according to the invention in which one end of the sleeve is folded upon itself to define a double-walled sleeve portion which is closed off by folding the opposite end of the sleeve upon the one end thereof.

FIG. 1 shows a longitudinal section of a known stent, indicated generally with the reference numeral 2 and of the type disclosed in my pending European patent applications EP-A-0 521 573 and EP-A-0 617 930, which are herein incorporated by reference.

The stent 2 comprises an elongated double-walled sleeve 4 of suitable foil material, for example teflon, which is closed on itself. In the space between the walls 6a, 6b of the sleeve 4, a curable material 8 is arranged. This curable material 8, such as a suitable acrylate, may be held in and supported by a mesh-like support structure in the manner described in EP-A-0 617 930. Such a stent may be introduced through a catheter to the desired emplacement location in a blood vessel by means of a carrier and positioning balloon. Subsequently, the balloon is expanded by supplying thereto an inflation medium under pressure, whereby the stent adopts ultimately a generally cylindrical form and adapts to the wall profile of a blood vessel. Then, the curable material is cured by irradiation with a suitable light-wave radiation such as laser or ultraviolet light radiation. When cured, the stent becomes dimensionally stable and is anchored in the blood vessel.

My application EP-A-0 617 930 describes one method for manufacturing such a stent. However, the invention has as its object to provide an improved method specifically suitable for large scale industrial manufacturing of stents of varying thickness, lengths and diameters.

Turning to FIG. 2, the starting point of the present invention begins with a hollow cylindrical sleeve 10 formed from a biocompatible foil material, such as teflon, which has a diameter d related to the diameter of the stent ultimately desired.

Figure 3A:
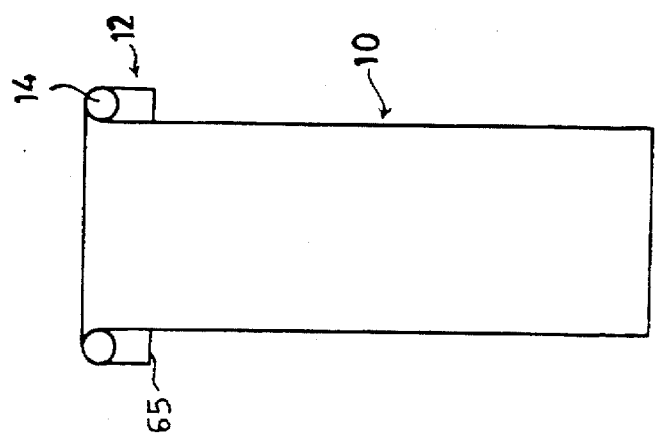
Figure 3E:
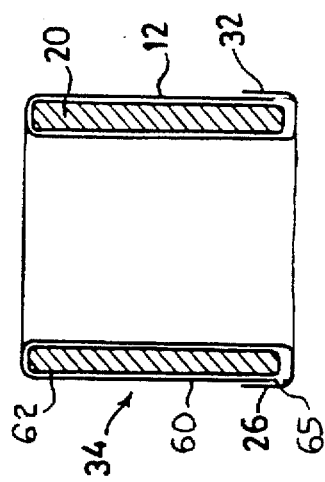

From this sleeve 10, a double-walled sleeve portion is formed. FIG. 3a shows how the formation of the double-walled sleeve portion is accomplished. The sleeve 10 is seem to have two opposite ends in the Figures. One end 65, illustrated toward the top of FIGS. 2 & 3, is folded, or curled outwardly over a circular guide member 14 which engages the sleeve 10. The one sleeve end 65 is pulled, or drawn, lengthwise over the sleeve in the direction of arrow 16 as shown in FIG. 3b. As the one end 65 is drawn over the guide member 14 lengthwise over the sleeve 10 as illustrated, it defines a skirt 60 which is extended for a predetermined length l, which may be chosen so as to approximate the desired length of the final stent.

Figure 3D:
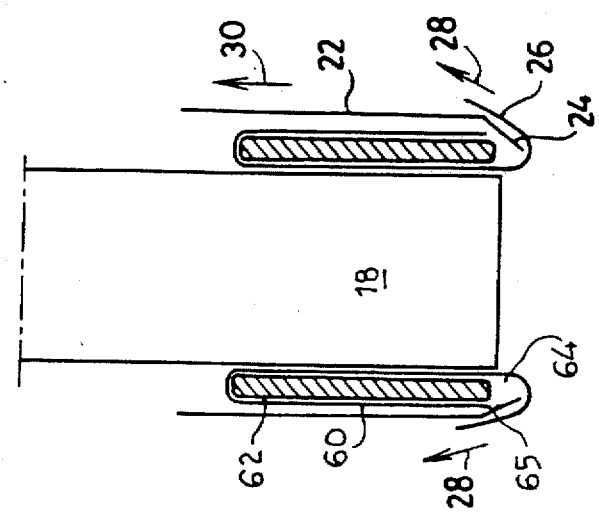
Figure 3C:
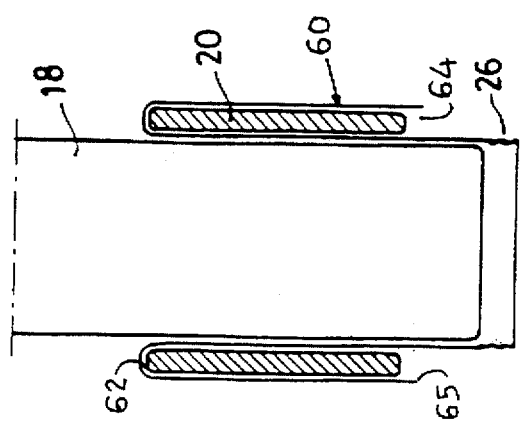

The skirt 60 and that portion of the sleeve 10 which opposes it cooperate to define an annular space 62 therebetween. The skirt 60 at this stage may be considered as forming the base of the outer wall of the finished stent. Once this initial fold has been established, the guide member 14 is withdrawn and the double-wall portion of the sleeve 10 may then be arranged on a mandrel 18. The mandrel 18 preferably extends for the entire length of the sleeve 10 as illustrated in FIG. 3c. A curable material 20, such as an acrylate which will harden upon expose to light-wave radiation of either a laser or ultra-violet light is then placed into the annular space 62 between the sleeve wall and the skirt 60. As mentioned in the above referenced EP-A-0 617 930 application, the curable material 8 may be placed upon a suitable mesh-like support and then inserted into the annular space 62.

A second guide, or curling, member 22 which has a circular or bent forward edge 24 at its end is advanced down around the mandrel 18 and outside of the outer wall of the sleeve, i.e. outside of the skirt 60. Once the curling member 22 is in place, the opposite free end 26 of the sleeve 10 is pulled upward in the direction of arrows 28 by a suitable gripping means (not shown), to thereby curl the free end 26 around the edge 24 of the member and around the opening 64 of the annular space 62. This in effect, encloses the curable material 20 in the annular space. The curling member 22 is removed by moving it in the direction of arrow 30 until the free end, or opposite end 26 of the sleeve closes around and abuts the outer wall 12a of the sleeve 10 as shown in FIG. 3d.

Finally, the edge 26 is fixed to the outer wall 12a in a manner known in the art at position 32 and the stent 34 is ready as illustrated in FIG. 3c to completely seal the curable material 20 in the annular space 62.

Forming the double-walled sleeve is also possible in the manner illustrated in FIGS. 4a-4b, such as by pulling the one end 41 of a sleeve 40 from the outside to the inside over a cylindrical guiding edge 42 in the direction of arrows 44 to define an interior skirt 43 which cooperates with the outer sleeve wall 45 to form a double-walled sleeve portion with an extending free end or edge 47 disposed at the one end 41 of the sleeve which is advanced past the opposite end 47 of the sleeve 10. The free end 47 is then folded over the annular space created after filling it with a curable material and attached thereto in the manner described above.

Figure 5C:
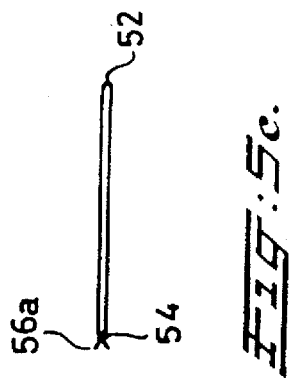
FIGS. 5a–5c show schematically a method for manufacturing the base sleeve of FIG. 2.
Figure 5B:
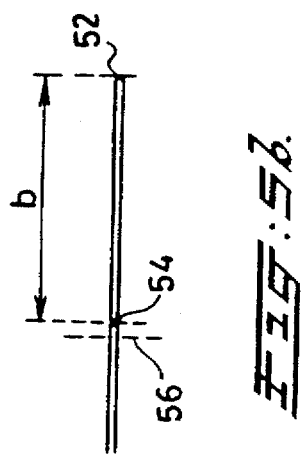
Figure 5A:
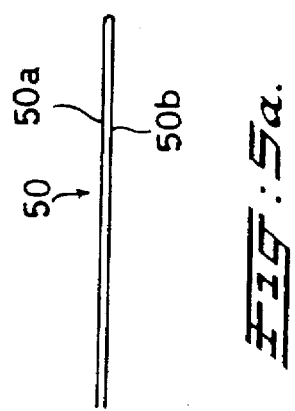

According to the invention, the starting sleeve 10 may be obtained by starting with a folded foil strip 50 as illustrated in FIG. 5a, wherein both parts 50a, 50b of the foil which lie on each other are connected to one another by a continuous elongate weld 54, at a distance b from the fold 52. This distance b is related to the diameter of the stent ultimately to be made according to $2b=\pi D$. The foil material is then cut at position 56, just beyond weld 54, resulting in the configuration illustrated in FIG. 5c so that the sleeve 58 has the configuration shown in FIG. 5c. In practice, the edges 56a extending over a short distance appear to produce absolutely no hindrance. This portion of the method is used to provide a single sleeve of double thickness.

It will be clear that the method as described above is specifically suitable for industrial manufacturing; one skilled in the art will be able to design the necessary auxiliary assembly elements such as the guide members, grippers, driving members, etc.

While the preferred embodiment of the invention have been shown and described, it will be understood by those skilled in the art the changes or modifications may be made thereto without departing from the true spirit and scope of the invention.

I claim:

1. A method for manufacturing an implantable stent having inner and outer walls enclosing a curable material, comprising the steps of:

forming a cylindrical sleeve from a biocompatible foil having a diameter approximately equal to the desired diameter of the implantable stent, the sleeve having opposing first and second ends;

grasping the first end of said sleeve and folding it onto itself so as to define a skirt which extends lengthwise along said sleeve which forms a double-wall sleeve portion, the second end of said sleeve extending lengthwise past said sleeve first end, said skirt and said sleeve cooperating to define an annular space therebetween;

inserting a curable material within the annular space along said double-wall sleeve portion;

grasping said second end of said sleeve and folding it back upon said first end of said sleeve to completely envelop said curable material with said sleeve and within said annular space thereof; and, connecting said sleeve second end to said sleeve proximate to said sleeve first end to seal said curable material within said sleeve.

2. The method according to claim 1, further including the steps of: providing a hollow first guide member around said sleeve; and, folding said sleeve first end over a free end of said guide member.

3. The method according to claim 1, further including the steps of: providing a curling guide member, placing the curling guide member over said double-wall sleeve portion; and, folding said sleeve second end over a free end of said curling guide to retain said curable material within said annular space prior to fixing said sleeve second end to said sleeve.

4. The method according to claim 1, wherein said sleeve first end is folded upon said sleeve by drawing said sleeve first end inwardly with respect to said sleeve.

5. The method according to claim 1, wherein said sleeve first end is folded upon said sleeve by drawing said sleeve first end outwardly with respect to said sleeve.

6. The method according to claim 1, further including the steps of: providing a hollow first guide member around said sleeve; folding said sleeve first end over a free end of said guide member; providing a hollow second guide member; placing the second guide member over said double-wall sleeve portion; and, folding said sleeve second end over a free end of said second guide member in order to retain said curable material within said annular space while folding said sleeve second end.

7. A stent obtained from the method of claim 1.

8. A method of forming an implantable stent for use in repair or reinforcement of blood vessels, the stent having a cylindrical, hollow tube-like configuration, the method comprising the steps of:

providing a thin strip of biocompatible material; forming the strip into a hollow sleeve of a given length having a single continuous sleevewall which defines an interior hollow passage of the sleeve, said sleeve having two opposing ends; folding the sleevewall onto itself by drawing one end of said sleeve around a guide and lengthwise upon said sleevewall for a predetermined length to define a double wall portion of said sleeve, the sleeve double wall portion having a length which is less than said sleeve given length, the double wall sleeve portion having an inner and outer wall and an annular space therebetween, said sleeve one end being spaced apart from an opposite end of said sleeve, the opposite end extending freely away from said sleeve one end; inserting a curable material into said annular space of said double wall sleeve portion; and, folding said sleeve opposite end onto said outer wall of said double wall sleeve portion; and, fixing said sleeve opposite end to said sleeve outer wall to completely enclose said curable material within said material.

9. The method of claim 8, wherein said guide member includes a circular ring member.

10. The method of claim 8, wherein said sleeve one end is folded upon said sleevewall by folding said sleeve one end outwardly upon said sleevewall to define said sleeve double wall portion.

11. The method of claim 8, wherein said sleeve one end is folded upon said sleevewall by folding said sleeve one end inwardly upon said sleevewall to define said sleeve double wall portion.

12. The method of claim 8, further including the steps of providing a curling guide; placing said curling guide over said sleevewall and engaging said sleeve near said sleeve opposite end; and, folding said sleeve one end onto said sleevewall to form said double wall sleeve portion.

13. The method of claim 8, wherein said curable material is a radiation-curable material.

14. The method of claim 8, wherein said curable material has a support matrix disposed therein.

15. The method of claim 8, wherein said curable material is in the form of a thick layer.

16. A stent formed by the method according to claim 8.

17. A method for manufacturing a stent, comprising forming a single wall sleeve from a biocompatible material, curling one end of the sleeve upon itself to form a skirt of predesired length extending upon the sleeve toward an opposite end thereof while leaving the opposite end of the sleeve free, the skirt and sleeve cooperating to define a double-wall portion of said sleeve having an annular space disposed between said skirt and said sleeve, filling the annular space so formed with a curable material, curling said sleeve opposite end up and over a portion of said skirt to enclose said curable material within said sleeve and fixing said opposite end of said sleeve to said skirt.

18. The method of claim 8, wherein said strip of biocompatible material includes a foil strip.

19. A method of forming an implantable stent for use in repair or reinforcement of blood vessels, the stent having a hollow cylindrical configuration, comprising the steps of:

providing an extent of stent material; forming the extent into a hollow sleeve of a given length having a sleeve wall that defines an interior hollow passage of the sleeve, said sleeve having first and second opposing ends; folding the sleeve wall onto itself by drawing the first end of said sleeve around a stent guide lengthwise upon said sleeve wall for a predetermined length to define a double wall portion of said sleeve, the double wall sleeve portion having distinct inner and outer walls separated by an annular space therebetween; inserting a curable material into said annular space; and, folding said sleeve second end onto said outer wall; and, fixing said sleeve second end to said outer wall to completely enclose said curable material within said foil.

20. The method of claim 19, further including the steps of providing an additional stent guide and folding said sleeve second end onto said sleeve wall by folding said sleeve second end over said additional stent guide.

* * * * *

UNITED STATES PATENT AND TRADEMARK OFFICE
CERTIFICATE OF CORRECTION

PATENT NO. : 5,741,324
DATED      : April 21, 1998
INVENTOR(S): Hendrik Glastra

It is certified that error appears in the above-identified patent and that said Letters Patent is hereby corrected as shown below:

Col. 1, line 21, "have a" should read --have an--; line 32, "forming a" should read --forming an--.
Col. 3, line 4, the "d" after "diameter" should be in bold; line 9, "seem to" should read --seen to--; line 17, the "l" after "length" should be in bold; line 28, delete "expose" and insert --exposure--.

Signed and Sealed this

Fourth Day of July, 2000

Attest:

Q. TODD DICKINSON

*Attesting Officer*       *Director of Patents and Trademarks*